United States Patent [19]

Ninomiya et al.

[11] Patent Number: 4,923,607
[45] Date of Patent: May 8, 1990

[54] MEMBRANE CONTAINING A LIQUID ACTIVE SUBSTANCE AND PROCESS FOR THE PRODUCTION OF SAME

[75] Inventors: Yasuo Ninomiya; Yoshikazu Musa; Yoichi Kainoh; Chiaki Komamura, all of Osaka, Japan

[73] Assignee: Nitto Denko Corporation, Osaka, Japan

[21] Appl. No.: 127,513

[22] Filed: Nov. 30, 1987

Related U.S. Application Data

[63] Continuation of Ser. No. 515,227, Jul. 19, 1983, abandoned.

[30] Foreign Application Priority Data

Aug. 16, 1982 [JP] Japan .................................. 57-141952

[51] Int. Cl.$^5$ .............................................. B01D 13/00
[52] U.S. Cl. .................................. 210/490; 210/500.41
[58] Field of Search ........................... 210/500.41, 490; 264/41, 49

[56] References Cited

U.S. PATENT DOCUMENTS

| | | | |
|---|---|---|---|
| 3,216,882 | 11/1965 | Feldt et al. | 210/44 X |
| 3,598,728 | 8/1971 | Bixler et al. | 210/645 X |
| 3,762,566 | 10/1973 | DelPico | 210/490 |
| 3,884,801 | 5/1975 | Kesting | 210/500.2 X |
| 3,923,939 | 12/1975 | Baker et al. | 264/4 X |
| 4,077,407 | 3/1978 | Theeuwes et al. | 264/49 |
| 4,138,344 | 2/1979 | Chol et al. | 252/1 |
| 4,248,855 | 2/1987 | Blank et al. | 424/19 |
| 4,353,962 | 10/1982 | Himel et al. | 264/4 X |
| 4,519,909 | 5/1985 | Castro | 210/500.27 |

OTHER PUBLICATIONS

Kirk-Othmer, *Encyclopedia of Chemical Technology*, 3rd Ed., Supplement, John Wiley & Sons, Inc., N.Y. (1984), pp. 643-644, 665.

*Primary Examiner*—Frank Spear
*Attorney, Agent, or Firm*—Sughrue, Mion, Zinn, Macpeak & Seas

[57] ABSTRACT

A liquid active substance-containing membrane having an anisotropic structure comprising (a) a polymeric cellular layer containing a myriad of minute closed cells and septa thereof and (b) a dense thin layer covering the surface of the cellular layer, wherein the minute cells contain therein a liquid active substance having a limited solubility in the polymer at normal temperature. The membrane of the present invention can be advantageously used to release a liquid active substance such as pheromones and pesticides at a substantially constant, controlled rate over a long period of time.

7 Claims, 5 Drawing Sheets

MEMBRANE CONTAINING A LIQUID ACTIVE SUBSTANCE AND PROCESS FOR THE PRODUCTION OF SAME

This is a continuation of application Ser. No. 515,227 filed 7/19/83 now abandoned.

FIELD OF THE INVENTION

The present invention relates to a membrane containing a liquid active substance. The membrane can be advantageously used to release a liquid active substance such as a pheromone or pesticide at a substantially constant, controlled rate over a long period of time. The present invention also relates to a process for the production of the membrane.

BACKGROUND OF THE INVENTION

There are several known articles used to release an active substance in a controlled manner. Such articles are usually made up of a carrier layer and a control layer as disclosed in, for example, U.S. Pat. No. 4,160,335. The carrier layer contains an active substance dissolved therein. The control layer, which covers the carrier layer, controls the permeation or diffusion of the active substance so that the active substance is released into the surrounding atmosphere at a substantially constant rate. When the active substance is a liquid, the carrier layer is prepared by uniformly dissolving the active substance in a polymer which is highly miscible with the active substance. Thus, the prepared carrier layer is covered by the control layer comprising a polymer which is less miscible with the active substance.

However, the above articles are disadvantageous in that the solubility of the active substance in the polymer used as the carrier layer is limited. Thus, it is usually difficult to have the carrier layer contain more than 30 wt % of the active substance. If a liquid active substance is dissolved in the polymer in an amount greater than 30 wt %, the polymer cannot form a solid matrix. Therefore, the content of the active substance in such articles is usually limited to about 10 wt %.

In order to overcome the above-disclosed disadvantage, a carrier layer which is composed of an open-cell porous polymer membrane and an active substance absorbed in the membrane has been used.

However, the above carrier layer is disadvantageous in that the surface of the carrier layer is made wet by the active substance. This makes it difficult to form a control layer thereon. Therefore, the carrier layer is usually enclosed in a membrane body which serves as the control layer. However, the use of membrane body is disadvantageous since it requires additional production steps which increases the cost of the articles.

SUMMARY OF THE INVENTION

An object of the present invention is to provide a membrane containing a liquid active substance.

A further object of the present invention is to provide a membrane useful for releasing a liquid active substance at a substantially constant, controlled rate.

The objects of the present invention have been met in one embodiment by a membrane having an anisotropic structure comprising (a) a cellular layer containing a myriad of minute closed cells and septa thereof and (b) a dense thin layer covering the surface of the cellular layer, wherein the cellular layer and dense thin layer together serve as the control layer.

Another embodiment of the present invention is to provide a process for the production of the membrane which comprises:

(1) dissolving a polymer and a liquid active substance in an organic solvent, wherein the liquid active substance has a limited solubility in the polymer at normal temperature, and wherein the organic solvent is capable of solubilizing both the liquid active substance and the polymer and is more volatile than the liquid active substance;

(2) applying the resulting solution to the surface of a support; and (3) evaporating the solvent of the solution so as to form a polymeric cellular layer containing a myriad of minute closed cells and septa thereof and a dense thin layer covering the surface of the cellular layer, wherein the minute cells contain therein the liquid active substance.

DETAILED DESCRIPTION OF THE INVENTION

Figure 1:
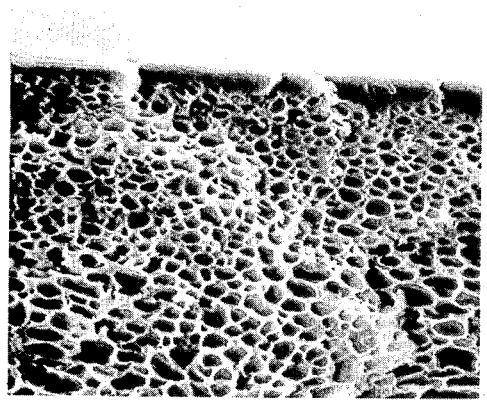
FIGS. 1 and 2 are scanning electron micrographs (magnification: ×1,300) of a cross section of the membrane of the present invention. These micrographs were taken after the liquid active substance contained in the membrane had been completely released.

The liquid active substance-containing membrane of the present invention has an anisotropic structure comprising (a) a polymeric cellular layer containing a myriad of independent minute cells and septa thereof and (b) a dense thin layer covering the surface of the cellular layer. The minute cells contain a liquid active substance which has a limited solubility in the polymer at normal temperature.

The liquid active substance used in the present invention is any liquid, at normal temperature, having chemical or physiological activity, e.g., pesticidal activity, attractant activity, repellent activity, and aromatic activity. Examples of such active substances include: (a) pesticides such as Naled, Diazinon, and Sumithion; (b) fungicides such as $\beta$-propiolactone; (c) repellents such as triethylene glycol monohexyl ether, and N,N-diethyl-m-toluamide; (d) attractants such as dodecyl acetate, Z-11-tetradecenyl acetate, and Z-11-hexadecenal; and (e) aromatic substances such as limonene and benzyl alcohol, and esters, ethers, and aldehydes derived from $C_6$-$C_{16}$ hydrocarbons.

The liquid active substance-containing membrane of the present invention has an anisotropic structure such that a dense thin layer on its surface is integrally supported on a cellular layer containing a myriad of minute closed cells and septa thereof. The cells range in size from 0.5 to 20 $\mu$m. Each cell is separated by a thin septum having a thickness from 0.1 to 10 $\mu$m. The liquid active substance is contained in the minute cells.

The thickness of the membrane is not specifically limited but it usually ranges from 10 to 500 $\mu$m. The membrane of the present invention can have an extremely high content of minute closed cells and thus it can contain up to about 70 wt % of a liquid active substance. The dense thin layer usually has a thickness of 0.1 to 200 μm, and preferably 1 to 100 μm.

According to the present invention, the liquid active substance to be contained in the membrane should have a limited solubility in the polymer constititing the membrane. The solubility means the maximum quantity (in parts by weight) of the liquid active substance that can be dissolved in 100 parts by weight of the polymer. The limited solubility means that the active substance is dissolved in an amount less than 5 parts by weight in 100 parts by weight of the polymer. A preferred polymer is capable of solubilizing the active substance in an amount of 0.01 to 1 wt %.

The polymer may be selected according to the liquid active substance to be used. Examples of such polymers include polysulfones, polyethersulfones, polycarbonates, polystyrene, polymethyl methacrylate and other poly(meth)acrylate esters, polyamides, polyvinylidene chloride, polyvinylidene fluoride, cellulose esters, regenerated cellulose, polyurethanes, polyvinyl alcohol, polyvinyl chloride, polyvinyl acetate, polyaryl esters, acrylonitrile-styrene copolymers, acrylonitrilestyrene-butadiene copolymers, ethylene-vinyl acetate copolymers, vinyl chloride-vinyl acetate copolymers, and polystyrene-polybutadiene block copolymers. The polymers may be used alone or in combination with one another.

The above-mentioned liquid substance-containing membrane is produced in the following manner.

A polymer and an active substance, which is liquid at normal temperature and has a limited solubility in the polymer, are dissolved in an organic solvent which solubilizes both the active substance and the polymer and is more volatile than the active substance. The resulting solution is applied to the surface of a support and the solvent is allowed to evaporate in order to form a polymeric cellular layer containing a myriad of minute closed cells and septa thereof and a dense thin layer covering the surface of the cellular layer wherein the minute cells contain the liquid active substance therein.

The organic solvent used in the present invention should solubilize both the active substance and the polymer and be more volatile or have a lower boiling point than the active substance. The organic solvent may be appropriately selected according to the type of the active substance and polymer to be employed. Examples of such organic solvents include methylene chloride, chloroform, carbon tetrachloride, and other halogenated aliphatic hydrocarbons; methanol, ethanol, and other lower aliphatic alcohols and acetate esters thereof; and acetonitrile, acetone, ethyl ether, and tetrahydrofuran. The organic solvents may be used alone or as combinations thereof. Halogenated lower aliphatic hydrocarbons such as methylene chloride are preferred organic solvents.

According to the process of the present invention, a liquid active substance and polymer are dissolved in an organic solvent as mentioned above. The resulting solution is applied to a support such as paper, plastic sheets, non-woven fabric sheets, and metal foils or laminates thereof, and the solvent is allowed to evaporate. The concentration of the total quantity of the liquid active substance and polymer in the solution is usually 10 to 40 wt %, and preferably 15 to 30 wt %.

The organic solvent may be evaporated at normal temperature or with heating if required.

Since the liquid active substance has a limited solubility in the polymer, a phase separation takes place between the active substance and the polymer as the evaporation of the organic solvent proceeds. Thus, minute droplets of the active substance are uniformly dispersed in the polymer matrix. Hence, the polymer forms a myriad of minute closed cells and the liquid active substance is enclosed in these minute cells. As the evaporation of the solvent proceeds, the concentration of the polymer increases at the surface of the applied solution and eventually a dense thin layer is formed which is integrated with the cellular layer composed of minute cells.

The minute cells formed in the membrane are separated by septa having a thickness of from 0.1 to 10 μm. The size of the cells is about 0.5 to 20 μm. Thus, the membrane has cell content of about 15 to 80%, and is capable of containing up to about 70 wt % of a liquid active substance. However, the content of the liquid active substance is preferably about 50 wt %.

Since the liquid active substance is limited in its solubility in the polymer and is covered by a dense thin layer, the liquid active substance in the minute cells diffuses into the polymer at a limited rate and the release of the liquid active substance into the atmosphere is controlled at a substantially constant rate by the surface dense thin layer. Thus, the membrane of the present invention is used for releasing an active substance at a controlled slow rate.

The present invention is now described in more detail with reference to the following non-limitative examples.

EXAMPLE 1

1 ml of Z-11-hexadecenal, an insect attractant, and 1 g of polysulfone were dissolved in 10 ml of methylene chloride. The resulting solution was applied at room temperature onto a support comprising a paper-aluminum laminate sheet. The methylene chloride was evaporated by allowing the article to stand at room temperature. In this manner a 40 μm thick membrane containing about 50 wt % of attractant was obtained.

After all of the attractant had been released, the cross section of the membrane was examined under a scanning electron microscope. An electron micrograph (magnification: ×1,300) thereof is shown in FIG. 1.

In the same manner as above except employing Z-11-tetradecenyl acetate, another insect attractant, instead of Z-11-hexadecenal, a 40 μm thick membrane containing about 50 wt % of Z-11-tetradecenyl acetate was obtained.

Figure 2:
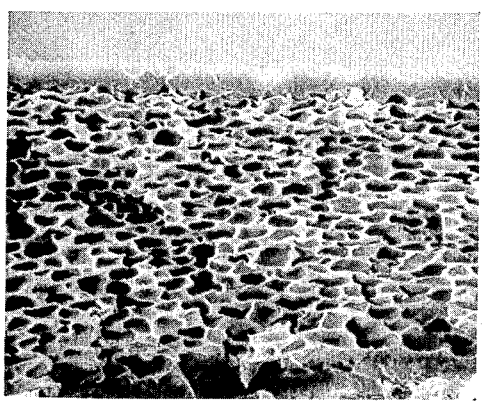

After all of the attractant had been released, the cross section of the membrane was examined under a scanning electron microscope. An electron micrograph (magnification: ×1,300) thereof is shown in FIG. 2.

The electron micrographs demonstrate that the minute cells in the membrane are 1 to 5 μm in size, the septa of the cells have a thickness of 0.2 to 0.5 μm, and the dense thin layer on the membrane has a thickness of 4 μm.

The solubility, as defined above, of Z-11-hexadecenal and Z-11-tetradecenyl acetate in polysulfone is 0.7 part by weight and 0.8 part by weight, respectively.

EXAMPLE 2

1 ml of dodecyl acetate, an insect attractant, and 1 g of polysulfone were dissolved in 10 ml of methylene chloride. The resulting solution was applied onto a support film at room temperature. The methylene chloride was evaporated by standing at room temperature.

In this manner, membranes of varying thicknesses containing about 50 wt % of attractant were obtained. The thicknesses of the membranes were 10 μm, 20 μm and 40 μm.

Figure 3:
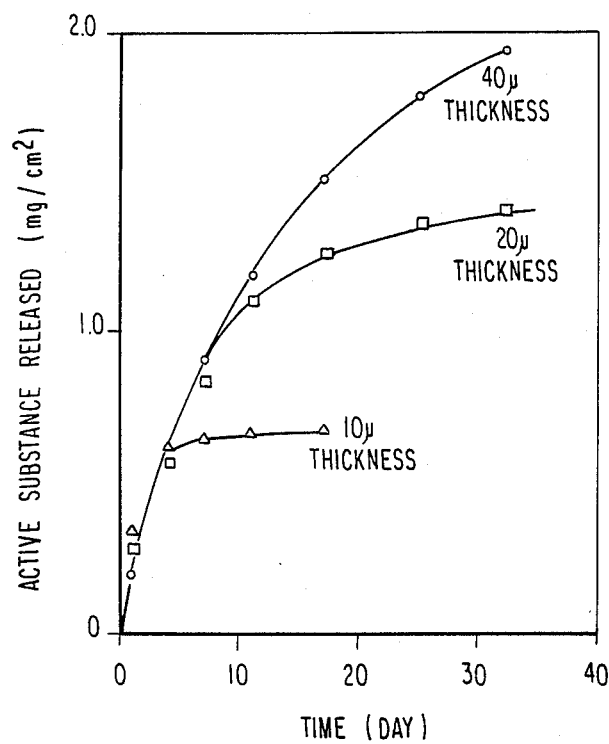
FIGS. 3 to 9 are graphs showing the release rate of a liquid active substance from the membrane of the present invention.

The release rate of the attractant at 25° C. was determined by measuring the decrease of the weight of the membrane. The results are shown in FIG. 3. FIG. 3 demonstrates that the release rate per unit area of the membrane is almost the same, but the thicker the membrane, the longer the period of release.

On the other hand, when the membranes were prepared, with the content of the attractant varying from 30 wt % to 70 wt %, it was observed that the higher the content of the attractant, the greater the release rate of the attractant.

This example demonstrates that the period of release of an active substance can be controlled by properly changing the thickness of the membrane. Further, it is also possible to control the release rate of an active substance by changing the content of an active substance in the membrane.

EXAMPLE 3

A varied quantity (1 ml, 0.5 ml, 0.2 ml and 0.1 ml) of Z-11-tetradecenyl acetate and 1 g of polysulfone were dissolved in 10 ml of methylene chloride. The resulting solution was applied onto a support film at room temperature and the solvent was evaporated. In this manner, four membranes, about 80 μm thick, containing about 50 wt %, 33 wt %, 17 wt %, and 9 wt % of pheromone were obtained. The dense thin layer formed on the surface of the resulting membrane was thicker in inverse proportion to the content of the pheromone. That is, it was about 8 μm, 20 μm, 40 μm and 70 μm.

Figure 4:
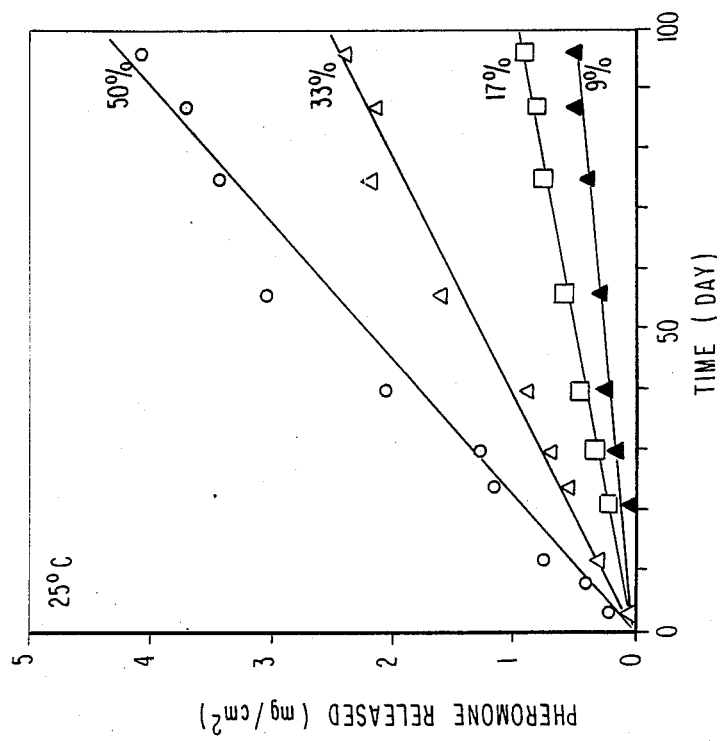

The release rate of the pheromone at 25° C. was determined by measuring the decrease of the weight of the membrane and by quantitative analyses of residual pheromone in the membrane. The results, as shown in FIG. 4, demonstrate that the release of the pheromone continued at almost a constant rate over a period of 100 days, but the thicker the dense thin layer, the lower the release rate.

EXAMPLE 4

1 ml of Z-11-tetradecenyl acetate and 1 g of polysulfone, polycarbonate or polymethyl methacrylate were dissolved in 10 ml of methylene chloride. The resulting solution was applied onto a support film at room temperature and the solvent was evaporated. In this manner, three membranes, about 40 μm thick, containing about 50 wt % of pheromone were obtained. The solubility of Z-11-tetradecenyl acetate in the above-mentioned three polymers is in the range of 0.2 to 0.8 part by weight.

Figure 5:
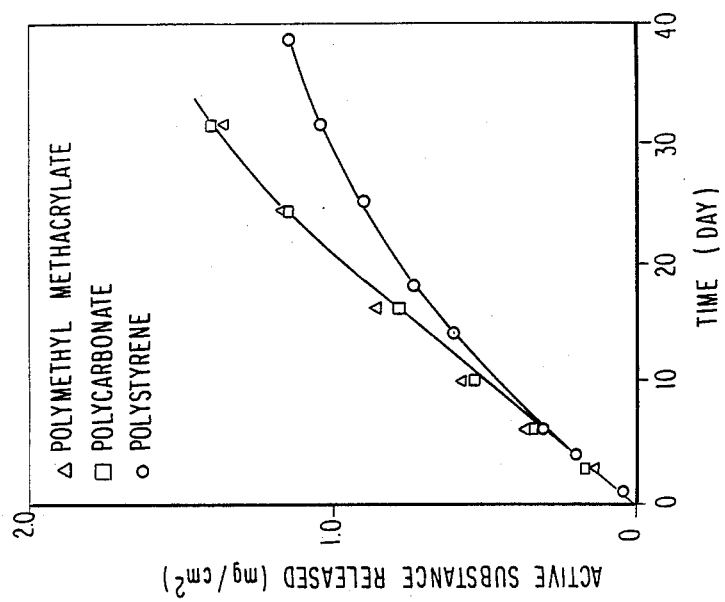

The release rate of the pheromone at 25° C. was determined by measuring the decrease of the weight of the membrane. The results, as shown in FIG. 5, demonstrate that the release rate was almost the same in all three membranes and the release of the pheromone continued over a period of 40 days.

EXAMPLE 5

1 ml of Z-11-tetradecenyl acetate and 1 g of cellulose triacetate were dissolved in 10 ml of methylene chloride. The resulting solution was applied onto a support film at room temperature and the solvent was evaporated. In this manner, a 40 μm thick membrane containing about 50 wt % of pheromone was obtained. The solubility of Z-11-tetradecenyl acetate in cellulose triacetate is in the range of 1.6 to 1.8 parts by weight.

Figure 6:
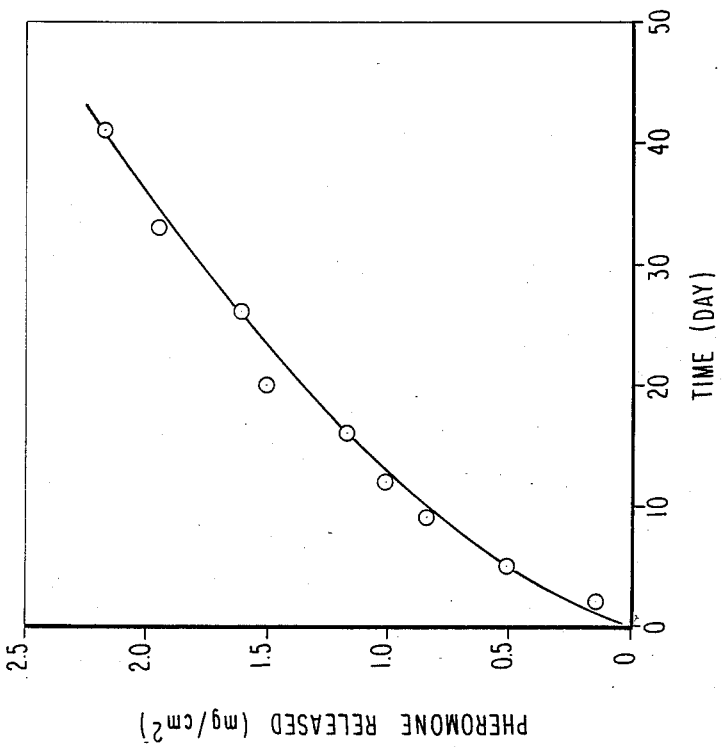

The release rate of the pheromone at 25° C. was determined by measuring the decrease in the weight of the membrane. The results, as shown in FIG. 6, demonstrate that the release rate was almost constant over a period of 40 days.

EXAMPLE 6

In the same manner as in Example 1, a 40 μm thick polysulfone membrane containing about 50 wt % of Z-11-hexadecenal was obtained.

The release rate of the attractant at 25° C. was measured in the same manner as in Example 1.

Figure 7:
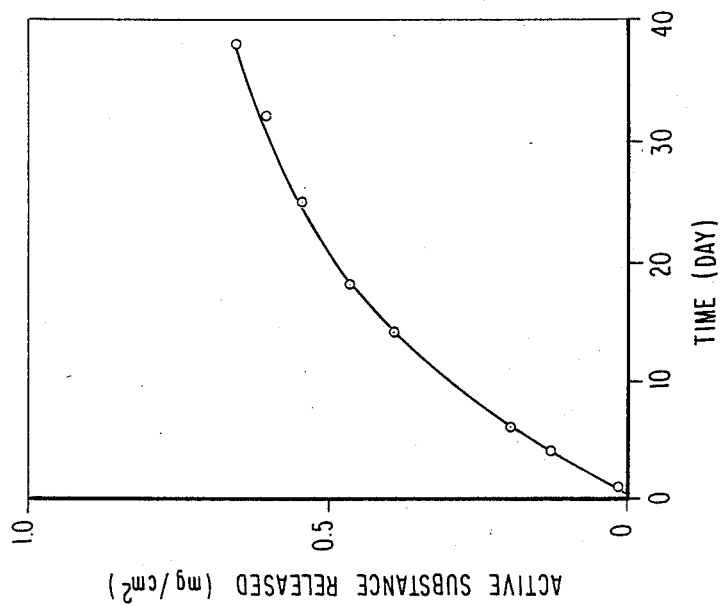

Since the attractant used in this example is an aldehyde, it is chemically unstable and is easily oxidized by oxidizing agents and/or ultraviolet light. Therefore, it is difficult to control the release rate. However, the results of this example, as shown in FIG. 7, demonstrate that the attractant was released at almost a constant rate over a period of 30 days.

EXAMPLE 7

1 ml of insecticides Naled, Diazinon, or Sumithion and 1 g of polycarbonate were dissolved in 10 ml of methylene chloride. Using the same procedure as in Example 1, three membranes, about 40 μm thick, containing about 50% of insecticide were obtained.

Figure 8:
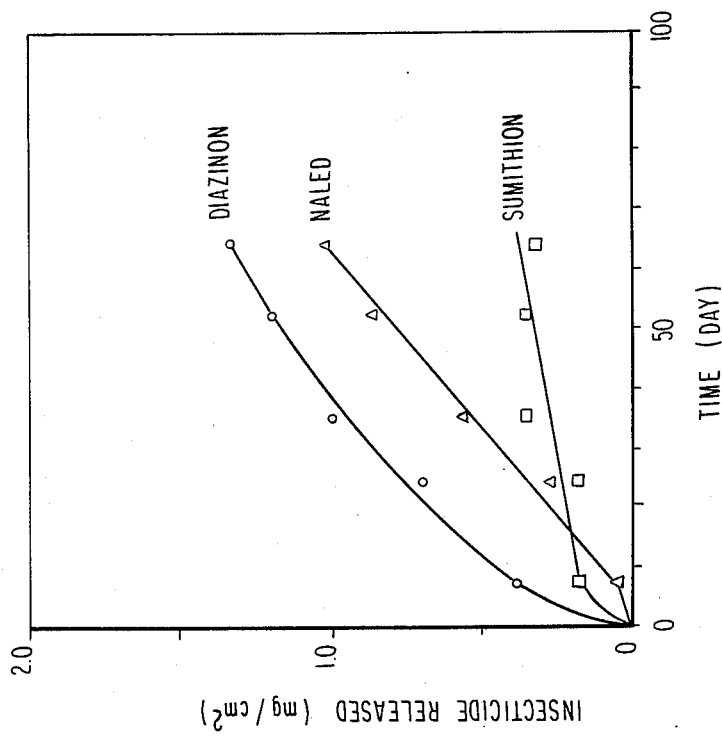

The release rate of the insecticide at 25° C. was measured by extracting the residual insecticide in the membrane with ethanol after a certain period of time. The results, as shown in FIG. 8, demonstrate that the insecticide was released at almost a constant rate over a long period of time.

When tested against the German cockroach (*Bluttela germanica*) as described below the membranes prepared in this example demonstrate an insecticidal effect over a long period of time. The membrane containing Naled was effective for more than 150 days.

The insecticidal effect was tested in the following manner:

An insecticide-containing membrane 9 cm in diameter was placed in a round plastic container. Ten adult German cockroaches were placed in the container. The time required for 50% of the cockroaches to fall unconscious was measured. The period in which this time was kept almost constant (about 5 hours in the case of Naled) was regarded as the effective period.

EXAMPLE 8

1 ml of triethylene glycol monohexyl ether, an insect repellent, and 1 g of polycarbonate were dissolved in 10 ml of methylene chloride. Using the same procedure as in Example 1, a 40 μm thick membrane containing about 50 wt % of repellent was obtained.

Figure 9:
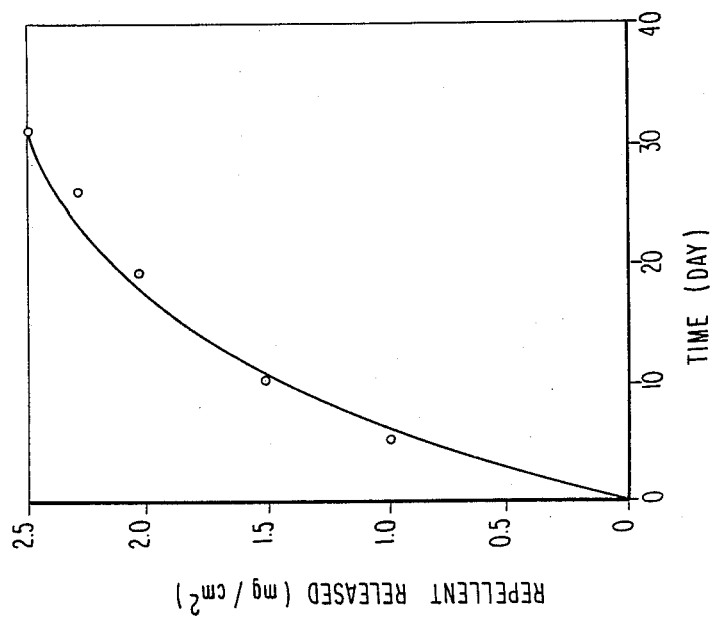

The release rate of the repellent was measured as in Example 1. The results, as shown in FIG. 9, demonstrate that the repellent was released at almost a constant rate over 30 days.

When tested against German cockroaches, in the manner described below, 90% of the repellent effect of the membrane prepared in this example was maintained for a period of over one month.

The repellent effect was tested in the following manner:

A sealed container measuring 500 mm wide, 400 mm deep, and 150 mm high was used as a testing box. A shelter was placed at the center of the left edge of the box. A cockroach trap ("Rotel", a product of Fumakilla Limited), with the membrane in the form of 2 cm wide tape adhered on the floor, was placed at the rear corner of the right edge of the box. Another cockroach trap of the same type containing an attracting bait was placed at the front corner of the right edge of the box. One hundred adult German cockroaches, which had been subjected to photoperiodic control and had been deprived of food for 3 days, were placed in the shelter. As soon as the light was turned out, the gate of the shelter was opened, and 2.5 hours later, the number of cockroaches that entered each cockroach trap was counted. The repelling ratio was calculated from the following equation.

$$\text{Repelling Ratio } (\%) = [(C-R)/(C+R)] \times 100$$

wherein C is the number of cockroaches caught in the control (i.e., where the membrane was not used), and R is the number of cockroaches caught when a repellent is used.

While this invention has been described in detail and with reference to specific embodiments thereof, it would be apparent to one skilled in the art that various changes and modifications can be made therein without departing from the spirit and scope thereof.

What is claimed is:

1. A liquid active substance-containing membrane having an anisotropic structure comprising (a) a polysulfone cellular layer containing a myriad of minute closed cells and septa thereof, (b) a dense thin layer covering one surface of the cellular layer and (c) a support provided on the surface of the cellular layer opposite the dense thin layer, wherein said minute cells contain a liquid active substance in the form of liquid droplets having a limited solubility in said polysulfone of less than 5 parts by weight per 100 parts by weight of the polysulfone at normal temperature, and wherein said liquid active substance in the minute cells diffuses into the polysulfone at a limited rate and the release of the liquid active substance into the atmosphere is controlled at a substantially constant rate by said surface dense thin layer.

2. A liquid active substance-containing membrane as claimed in claim 1, wherein the minute cells of the cellular layer have a diameter of 0.5 to 20 $\mu$m and the septa of the cells have a thickness of 0.1 to 10 $\mu$m.

3. A liquid active substance-containing membrane as claimed in claim 1, wherein the dense thin layer has a thickness of 0.1 to 100 $\mu$m.

4. A liquid active substance-containing membrane as claimed in claim 1, wherein the limited solubility of the liquid active substance in the polysulfone is 0.01 to 2 parts by weight per 100 parts by weight of the polysulfone.

5. A liquid active substance-containing membrane as claimed in claim 1, wherein the liquid active substance is a liquid substance at normal temperature which has chemical or physiological activity.

6. A liquid active substance-containing membrane as claimed in claim 5, wherein said chemical or physiological activity is pesticidal activity, attractant activity, or aromatic activity.

7. A liquid active substance-containing membrane having an anisotropic structure comprising (a) a polysulfone cellular layer containing a myriad of minute closed cells and septa thereof, (b) a dense thin layer covering one surface of the cellular layer and (c) a support provided on the surface of the cellular layer opposite the dense thin layer, wherein said minute cells contain a liquid active substance having a limited solubility in said polysulfone of less than 5 parts by weight per 100 parts by weight of the polysulfone at normal temperature and in the form of liquid droplets, wherein the minute cells of the cellular layer have a diameter of 0.5 to 20 $\mu$m, the septa of the cells have a thickness of 0.1 to 10 $\mu$m and the dense thin layer has a thickness of 0.1 to 100 $\mu$m and wherein said liquid active substance in the minute cells diffuses into the polysulfone at a limited rate and the release of the liquid active substance into the atmosphere is controlled at a substantially constant rate by said surface dense thin layer.

* * * * *